United States Patent [19]
Briles et al.

[11] Patent Number: 5,965,141
[45] Date of Patent: *Oct. 12, 1999

[54] EPITOPIC REGIONS OF PNEUMOCOCCAL SURFACE PROTEIN A

[75] Inventors: David E. Briles; Janet L. Yother; Larry S. McDaniel; Hong-Yin Wu, all of Birmingham, Ala.

[73] Assignee: UAB Research Foundation, Birmingham, Ala.

[*] Notice: This patent is subject to a terminal disclaimer.

[21] Appl. No.: 08/246,636

[22] Filed: May 20, 1994

Related U.S. Application Data

[63] Continuation-in-part of application No. 08/048,896, Apr. 20, 1993, abandoned, which is a continuation-in-part of application No. 07/835,698, Feb. 12, 1992, abandoned, which is a continuation-in-part of application No. 07/656,773, Feb. 15, 1991, abandoned.

[51] Int. Cl.$^6$ .................................................. A61K 39/09
[52] U.S. Cl. .................................. 424/244.1; 424/237.1; 530/350; 435/69.1; 435/320.1
[58] Field of Search ...................... 530/350, 820; 424/237.1, 244.1; 435/320.1, 69.1

[56] References Cited

U.S. PATENT DOCUMENTS

| | | | |
|---|---|---|---|
| 4,496,538 | 1/1985 | Gordon | 424/92 |
| 4,554,101 | 11/1985 | Hopp | 260/112.5 |
| 4,673,574 | 6/1987 | Anderson | 424/92 |
| 4,847,080 | 7/1989 | Neurath et al. | 424/89 |
| 5,142,027 | 8/1992 | Domen et al. | 530/363 |

FOREIGN PATENT DOCUMENTS

WO 92/14488  3/1992  WIPO.

OTHER PUBLICATIONS

Abstract of the 92nd General Meeting of the American Society for Microbiology, vol. 0, 1992, Abstract B–268 p. 70, Briles, D.E. et al. Mapping Protection Eliciting Epitopes of Pneumococcal Surface Protein A (PspA).
Microbial Pathogenesis, vol. 17, Nov. 1994 Aberdeen GB, pp. 323–337, McDaniel L.S. et al. Localization of Protection–Eliciting Epitopes on PspA of Streptococcus Pneumoniae between Amino acid Residues 192 and 260).
The Journal of Experimental Medicine, vol. 163, No. 6 1986 New York, pp. 1451–1458, Beachy E.H. et al., "Opsonic Antibodies Evoked by Hybrid Peptide Copies of Type 5 and 24 Streptococcal M Proteins Synthesized in Tandem".
McDaniel et al (I), J.Exp.Med. 160:386–397, 1984.
McDaniel et al (II), Microbial Pathogenesis 1:519–531, 1986.
McDaniel et al (III), J.Exp.Med. 165:381–394, 1987.
McDaniel et al (IV), Infect. Immun., 59:222–228, 1991.
Crain et al, Infect.Immun., 58:3293–3299, 1990.
Abstracts of 89th Annual Meeting of the American Society for Microbiology, p. 125, item D–257, May 1989.
Abstracts of 90th Annual Meeting of the American Society for Microbiology, p. 98, item D–106, May 1990.
Abstract of 3rd International ASM Conference on Streptococcal Genetics, p. 11, item 12, Jun. 1990.
Talkington et al, Infect. Immun. 59:1285–1289, 1991.
Yother et al, J. Bacteriol. 174:601–609, 1992.
Yother et al, J. Bacteriol. 174:610–618, 1992.
McDaniel et al (V), Microbiol Pathogenesis, 13:261–268.
Stover et al. "New use of BCG for recombinant vaccines" Nature (351) 456–460, Jun. 1991.
R. Young and R. Davis, Proc. Natnl. Acad. Sci., 80: pp. 1194–1198, 1983.
"Anitbodies, A Laboratory Manuel", E. Harlow and D. Lane, See Chapter 13, pp. 511–551, 1988.
Ponger et al., Methods in Enzymology, 154: 450–473, 1987.
Rijn et al., "Growth Characteristics of Group A Streptococci in a New Chemically Defined Medium", Infec. and Immun., pp. 444–448, Feb. 1980.

*Primary Examiner*—James C. Housel
*Assistant Examiner*—Jennifer Graser
*Attorney, Agent, or Firm*—Frommer Lawrence & Haug LLP; William S. Frommer; Thomas J. Kowalski

[57] ABSTRACT

A region of the PspA protein of the Rx1 strain of *Streptococcus pneumoniae* has been identified as containing protection-eliciting epitopes which are cross-reactive with PspAs of other *S. pneumoniae* strains and which is cross-protective. The region comprises the 68-amino acid sequence extending from amino acid residues 192 to 260 of the Rx1 PspA strain.

35 Claims, 6 Drawing Sheets

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:

```
        (A) LENGTH: 2085 base pairs
        (B) TYPE: nucleic acid
        (C) STRANDEDNESS: double
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Streptococcus pneumoniae
        (B) STRAIN: Rx1

(vii) IMMEDIATE SOURCE:
        (B) CLONE: JY4313

(ix) FEATURE:
        (A) NAME/KEY: intron
        (B) LOCATION: 1..2085

(ix) FEATURE:
        (A) NAME/KEY: CDS
        (B) LOCATION: join(127..1984)

(xi) SEQUENCE DESCRIPTION: SEQ ID NO:1:

AAGCTTATGA TATAGAAATT TGTAACAAAA ATGTAATATA AAACACTTGA CAAATATTTA     60

CGGAGGAGGC TTATACTTAA TATAAGTATA GTCTGAAAAT GACTATCAGA AAAGAGGTAA    120

ATTTAG ATG AAT AAG AAA AAA ATG ATT TTA ACA AGT CTA GCC AGC GTC      168
       Met Asn Lys Lys Lys Met Ile Leu Thr Ser Leu Ala Ser Val
        1               5                  10

CCT ATC TTA GGG GCT GGT TTT GTT GCG TCT CAG CCT ACT GTT GTA AGA    216
Ala Ile Leu Gly Ala Gly Phe Val Ala Ser Gln Pro Thr Val Val Arg
 15              20                  25                  30

GCA GAA GAA TCT CCC GTA GCC AGT CAG TCT AAA GCT GAG AAA GAC TAT    264
Ala Glu Glu Ser Pro Val Ala Ser Gln Ser Lys Ala Glu Lys Asp Tyr
                 35                  40                  45

GAT GCA GCG AAG AAA GAT GCT AAG AAT GCG AAA AAA GCA GTA GAA GAT    312
Asp Ala Ala Lys Lys Asp Ala Lys Asn Ala Lys Lys Ala Val Glu Asp
             50                  55                  60

GCT CAA AAG GCT TTA GAT GAT GCA AAA GCT GCT CAG AAA AAA TAT GAC    360
Ala Gln Lys Ala Leu Asp Asp Ala Lys Ala Ala Gln Lys Lys Tyr Asp
         65                  70                  75

GAG GAT CAG AAG AAA ACT GAG GAG AAA GCC GCG CTA GAA AAA GCA GCG    408
Glu Asp Gln Lys Lys Thr Glu Glu Lys Ala Ala Leu Glu Lys Ala Ala
     80                  85                  90

TCT GAA GAG ATG GAT AAG GCA GTG GCA GCA GTT CAA CAA GCG TAT CTA    456
Ser Glu Glu Met Asp Lys Ala Val Ala Ala Val Gln Gln Ala Tyr Leu
 95                 100                 105                 110

GCC TAT CAA CAA GCT ACA GAC AAA GCC GCA AAA GAC GCA GCA GAT AAG    504
Ala Tyr Gln Gln Ala Thr Asp Lys Ala Ala Lys Asp Ala Ala Asp Lys
                115                 120                 125

ATG ATA GAT GAA GCT AAG AAA CGC GAA GAA GAG GCA AAA ACT AAA TTT    552
Met Ile Asp Glu Ala Lys Lys Arg Glu Glu Glu Ala Lys Thr Lys Phe
            130                 135                 140

AAT ACT GTT CGA GCA ATG GTA GTT CCT GAG CCA GAG CAG TTG GCT GAG    600
Asn Thr Val Arg Ala Met Val Val Pro Glu Pro Glu Gln Leu Ala Glu
        145                 150                 155

ACT AAG AAA AAA TCA GAA GAA GCT AAA CAA AAA GCA CCA GAA CTT ACT    648
Thr Lys Lys Lys Ser Glu Glu Ala Lys Gln Lys Ala Pro Glu Leu Thr
    160                 165                 170

AAA AAA CTA GAA GAA GCT AAA GCA AAA TTA GAA GAG GCT GAG AAA AAA    696
Lys Lys Leu Glu Glu Ala Lys Ala Lys Leu Glu Glu Ala Glu Lys Lys
175                 180                 185                 190
```

-continued

| | | |
|---|---|---|
| GCT ACT GAA GCC AAA CAA AAA GTG GAT GCT GAA GAA GTC GCT CCT CAA<br>Ala Thr Glu Ala Lys Gln Lys Val Asp Ala Glu Glu Val Ala Pro Gln<br>                195                              200                      205 | 744 |
| GCT AAA ATC GCT GAA TTG GAA AAT CAA GTT CAT AGA CTA GAA CAA GAG<br>Ala Lys Ile Ala Glu Leu Glu Asn Gln Val His Arg Leu Glu Gln Glu<br>              210                              215                        220 | 792 |
| CTC AAA GAG ATT GAT GAG TCT GAA TCA GAA GAT TAT GCT AAA GAA GGT<br>Leu Lys Glu Ile Asp Glu Ser Glu Ser Glu Asp Tyr Ala Lys Glu Gly<br>                  225                            230                        235 | 840 |
| TTC CGT GCT CCT CTT CAA TCT AAA TTG GAT GCC AAA AAA GCT AAA CTA<br>Phe Arg Ala Pro Leu Gln Ser Lys Leu Asp Ala Lys Lys Ala Lys Leu<br>        240                            245                              250 | 888 |
| TCA AAA CTT GAA GAG TTA AGT GAT AAG ATT GAT GAG TTA GAC GCT GAA<br>Ser Lys Leu Glu Glu Leu Ser Asp Lys Ile Asp Glu Leu Asp Ala Glu<br>255                          260                              265                        270 | 936 |
| ATT GCA AAA CTT GAA GAT CAA CTT AAA GCT GCT GAA GAA AAC AAT AAT<br>Ile Ala Lys Leu Glu Asp Gln Leu Lys Ala Ala Glu Glu Asn Asn Asn<br>                  275                            280                        285 | 984 |
| GTA GAA GAC TAC TTT AAA GAA GGT TTA GAG AAA ACT ATT GCT GCT AAA<br>Val Glu Asp Tyr Phe Lys Glu Gly Leu Glu Lys Thr Ile Ala Ala Lys<br>                      290                            295                        300 | 1032 |
| AAA GCT GAA TTA GAA AAA ACT GAA GCT GAC CTT AAG AAA GCA GTT AAT<br>Lys Ala Glu Leu Glu Lys Thr Glu Ala Asp Leu Lys Lys Ala Val Asn<br>        305                            310                              315 | 1080 |
| GAG CCA GAA AAA CCA GCT CCA GCT CCA GAA ACT CCA GCC CCA GAA GCA<br>Glu Pro Glu Lys Pro Ala Pro Ala Pro Glu Thr Pro Ala Pro Glu Ala<br>320                          325                              330 | 1128 |
| CCA GCT GAA CAA CCA AAA CCA GCG CCG GCT CCT CAA CCA GCT CCC GCA<br>Pro Ala Glu Gln Pro Lys Pro Ala Pro Ala Pro Gln Pro Ala Pro Ala<br>335                          340                              345                        350 | 1176 |
| CCA AAA CCA GAG AAG CCA GCT GAA CAA CCA AAA CCA GAA AAA ACA GAT<br>Pro Lys Pro Glu Lys Pro Ala Glu Gln Pro Lys Pro Glu Lys Thr Asp<br>                      355                            360                        365 | 1224 |
| GAT CAA CAA GCT GAA GAA GAC TAT GCT CGT AGA TCA GAA GAA GAA TAT<br>Asp Gln Gln Ala Glu Glu Asp Tyr Ala Arg Arg Ser Glu Glu Glu Tyr<br>                  370                            375                        380 | 1272 |
| AAT CGC TTG ACT CAA CAG CAA CCG CCA AAA GCT GAA AAA CCA GCT CCT<br>Asn Arg Leu Thr Gln Gln Gln Pro Pro Lys Ala Glu Lys Pro Ala Pro<br>        385                            390                              395 | 1320 |
| GCA CCA AAA ACA GGC TGG AAA CAA GAA AAC GGT ATG TGG TAC TTC TAC<br>Ala Pro Lys Thr Gly Trp Lys Gln Glu Asn Gly Met Trp Tyr Phe Tyr<br>400                          405                              410 | 1368 |
| AAT ACT GAT GGT TCA ATG GCG ACA GGA TGG CTC CAA AAC AAC GGT TCA<br>Asn Thr Asp Gly Ser Met Ala Thr Gly Trp Leu Gln Asn Asn Gly Ser<br>415                          420                              425                        430 | 1416 |
| TGG TAC TAC CTC AAC AGC AAT GGT GCT ATG GCT ACA GGT TGG CTC CAA<br>Trp Tyr Tyr Leu Asn Ser Asn Gly Ala Met Ala Thr Gly Trp Leu Gln<br>                  435                            440                        445 | 1464 |
| TAC AAT GGT TCA TGG TAT TAC CTC AAC GCT AAC GGC GCT ATG GCA ACA<br>Tyr Asn Gly Ser Trp Tyr Tyr Leu Asn Ala Asn Gly Ala Met Ala Thr<br>                    450                            455                        460 | 1512 |
| GGT TGG GCT AAA GTC AAC GGT TCA TGG TAC TAC CTC AAC GCT AAT GGT<br>Gly Trp Ala Lys Val Asn Gly Ser Trp Tyr Tyr Leu Asn Ala Asn Gly<br>                      465                            470                        475 | 1560 |
| GCT ATG GCT ACA GGT TGG CTC CAA TAC AAC GGT TCA TGG TAT TAC CTC<br>Ala Met Ala Thr Gly Trp Leu Gln Tyr Asn Gly Ser Trp Tyr Tyr Leu<br>480                          485                              490 | 1608 |
| AAC GCT AAC GGC GCT ATG GCA ACA GGT TGG GCT AAA GTC AAC GGT TCA<br>Asn Ala Asn Gly Ala Met Ala Thr Gly Trp Ala Lys Val Asn Gly Ser<br>495                          500                              505                        510 | 1656 |

-continued

```
TGG TAC TAC CTC AAC GCT AAT GGT GCT ATG GCT ACA GGT TGG CTC CAA      1704
Trp Tyr Tyr Leu Asn Ala Asn Gly Ala Met Ala Thr Gly Trp Leu Gln
                515                 520                 525

TAC AAC GGT TCA TGG TAC TAC CTC AAC GCT AAC GGT GCT ATG GCT ACA      1752
Tyr Asn Gly Ser Trp Tyr Tyr Leu Asn Ala Asn Gly Ala Met Ala Thr
            530                 535                 540

GGT TGG GCT AAA GTC AAC GGT TCA TGG TAC TAC CTC AAC GCT AAT GGT      1800
Gly Trp Ala Lys Val Asn Gly Ser Trp Tyr Tyr Leu Asn Ala Asn Gly
        545                 550                 555

GCT ATG GCA ACA GGT TGG GTG AAA GAT GGA GAT ACC TGG TAC TAT CTT      1848
Ala Met Ala Thr Gly Trp Val Lys Asp Gly Asp Thr Trp Tyr Tyr Leu
    560                 565                 570

GAA GCA TCA GGT GCT ATG AAA GCA AGC CAA TGG TTC AAA GTA TCA GAT      1896
Glu Ala Ser Gly Ala Met Lys Ala Ser Gln Trp Phe Lys Val Ser Asp
575                 580                 585                 590

AAA TGG TAC TAT GTC AAT GGT TTA GGT GCC CTT GCA GTC AAC ACA ACT      1944
Lys Trp Tyr Tyr Val Asn Gly Leu Gly Ala Leu Ala Val Asn Thr Thr
                595                 600                 605

GTA GAT GGC TAT AAA GTC AAT GCC AAT GGT GAA TGG GTT TAA GCC GAT      1992
Val Asp Gly Tyr Lys Val Asn Ala Asn Gly Glu Trp Val *
            610                 615

TAA ATT AAA GCA TGT TAA GAA CAT TTG ACA TTT TAA TTT TGA AAC AAA      2040

GAT AAG GTT CGA TTG AAT AGA TTT ATG TTC GTA TTC TTT AGG TAC          2085
```

(2) INFORMATION FOR SEQ ID NO:2:

(i) SEQUENCE CHARACTERISTICS:
        (A) LENGTH: 619 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Lys Lys Lys Met Ile Leu Thr Ser Leu Ala Ser Val Ala Ile
 1               5                  10                  15

Leu Gly Ala Gly Phe Val Ala Ser Gln Pro Thr Val Val Arg Ala Glu
                20                  25                  30

Glu Ser Pro Val Ala Ser Gln Ser Lys Ala Glu Lys Asp Tyr Asp Ala
            35                  40                  45

Ala Lys Lys Asp Ala Lys Asn Ala Lys Lys Ala Val Glu Asp Ala Gln
        50                  55                  60

Lys Ala Leu Asp Asp Ala Lys Ala Gln Lys Lys Tyr Asp Glu Asp
 65                  70                  75                  80

Gln Lys Lys Thr Glu Glu Lys Ala Ala Leu Glu Lys Ala Ala Ser Glu
                85                  90                  95

Glu Met Asp Lys Ala Val Ala Ala Val Gln Gln Ala Tyr Leu Ala Tyr
               100                 105                 110

Gln Gln Ala Thr Asp Lys Ala Ala Lys Asp Ala Ala Asp Lys Met Ile
        115                 120                 125

Asp Glu Ala Lys Lys Arg Glu Glu Glu Ala Lys Thr Lys Phe Asn Thr
    130                 135                 140

Val Arg Ala Met Val Val Pro Glu Pro Glu Gln Leu Ala Glu Thr Lys
145                 150                 155                 160

Lys Lys Ser Glu Glu Ala Lys Gln Lys Ala Pro Glu Leu Thr Lys Lys
                165                 170                 175

Leu Glu Glu Ala Lys Ala Lys Leu Glu Glu Ala Glu Lys Lys Ala Thr
            180                 185                 190
```

-continued

Glu Ala Lys Gln Lys Val Asp Ala Glu Val Ala Pro Gln Ala Lys
        195                 200                 205

Ile Ala Glu Leu Glu Asn Gln Val His Arg Leu Glu Gln Glu Leu Lys
    210                 215                 220

Glu Ile Asp Glu Ser Ser Glu Asp Tyr Ala Lys Glu Gly Phe Arg
225                 230                 235                 240

Ala Pro Leu Gln Ser Lys Leu Asp Ala Lys Ala Lys Leu Ser Lys
                245                 250                 255

Leu Glu Glu Leu Ser Asp Lys Ile Asp Glu Leu Asp Ala Glu Ile Ala
                260                 265                 270

Lys Leu Glu Asp Gln Leu Lys Ala Ala Glu Glu Asn Asn Asn Val Glu
        275                 280                 285

Asp Tyr Phe Lys Glu Gly Leu Glu Lys Thr Ile Ala Ala Lys Lys Ala
        290                 295                 300

Glu Leu Glu Lys Thr Glu Ala Asp Leu Lys Lys Ala Val Asn Glu Pro
305                 310                 315                 320

Glu Lys Pro Ala Pro Ala Pro Glu Thr Pro Ala Pro Glu Ala Pro Ala
                325                 330                 335

Glu Gln Pro Lys Pro Ala Pro Ala Pro Gln Pro Ala Pro Ala Pro Lys
                340                 345                 350

Pro Glu Lys Pro Ala Glu Gln Pro Lys Pro Glu Lys Thr Asp Asp Gln
        355                 360                 365

Gln Ala Glu Glu Asp Tyr Ala Arg Arg Ser Glu Glu Tyr Asn Arg
        370                 375                 380

Leu Thr Gln Gln Gln Pro Pro Lys Ala Glu Lys Pro Ala Pro Ala Pro
385                 390                 395                 400

Lys Thr Gly Trp Lys Gln Glu Asn Gly Met Trp Tyr Phe Tyr Asn Thr
                405                 410                 415

Asp Gly Ser Met Ala Thr Gly Trp Leu Gln Asn Asn Gly Ser Trp Tyr
                420                 425                 430

Tyr Leu Asn Ser Asn Gly Ala Met Ala Thr Gly Trp Leu Gln Tyr Asn
        435                 440                 445

Gly Ser Trp Tyr Tyr Leu Asn Ala Asn Gly Ala Met Ala Thr Gly Trp
        450                 455                 460

Ala Lys Val Asn Gly Ser Trp Tyr Tyr Leu Asn Ala Asn Gly Ala Met
465                 470                 475                 480

Ala Thr Gly Trp Leu Gln Tyr Asn Gly Ser Trp Tyr Tyr Leu Asn Ala
                485                 490                 495

Asn Gly Ala Met Ala Thr Gly Trp Ala Lys Val Asn Gly Ser Trp Tyr
                500                 505                 510

Tyr Leu Asn Ala Asn Gly Ala Met Ala Thr Gly Trp Leu Gln Tyr Asn
        515                 520                 525

Gly Ser Trp Tyr Tyr Leu Asn Ala Asn Gly Ala Met Ala Thr Gly Trp
        530                 535                 540

Ala Lys Val Asn Gly Ser Trp Tyr Tyr Leu Asn Ala Asn Gly Ala Met
545                 550                 555                 560

Ala Thr Gly Trp Val Lys Asp Gly Asp Thr Trp Tyr Tyr Leu Glu Ala
                565                 570                 575

Ser Gly Ala Met Lys Ala Ser Gln Trp Phe Lys Val Ser Asp Lys Trp
        580                 585                 590

Tyr Tyr Val Asn Gly Leu Gly Ala Leu Ala Val Asn Thr Thr Val Asp
        595                 600                 605

Gly Tyr Lys Val Asn Ala Asn Gly Glu Trp Val
        610                 615

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GCGCGTCGAC GGCTTAAACC CATTCACCAT TGG      33

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CCGGATCCTG AGCCAGAGCA GTTGGCTG      28

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CCGGATCCGC TCAAAGAGAT TGATGAGTCT G      31

EPITOPIC REGIONS OF PNEUMOCOCCAL SURFACE PROTEIN A

REFERENCE TO RELATED APPLICATION

This application is a continuation-in-part of U.S. patent application Ser. No. 08/048,896 filed Apr. 20, 1993, now abandoned, which itself is a continuation-in-part of U.S. patent application Ser. No. 07/835,698 filed Feb. 12, 1992, now abandoned, which itself is a continuation-in-part of Ser. No. 07/656,773 filed Feb. 15, 1991, now abandoned.

FIELD OF INVENTION

This invention relates to recognition of epitopic regions of pneumococcal surface protein A (PspA), the major virulence factor of Streptococcus pneumoniae.

BACKGROUND TO THE INVENTION

Streptococcus pneumoniae is an important cause of otitis media, meningitis, bacteremia and pneumonia. Despite the use of antibiotics and vaccines, the prevalence of pneumococcal infections has declined little over the last twenty-five years.

It is generally accepted that immunity to Streptococcus pneumoniae can be mediated by specific antibodies against the polysaccharide capsule of the pneumococcus. However, neonates and young children fail to make an immune response against polysaccharide antigens and can have repeated infections involving the same capsular serotype.

One approach to immunizing infants against a number of encapsulated bacteria is to conjugate the capsular polysaccharide antigens to proteins to make then immunogenic. This approach has been successful, for example, with Haemophilus influenzae b (see U.S. Pat. No. 4,496,538 to Gordon and U.S. Pat. No. 4,673,574 to Anderson). However, there are over eighty known capsular serotypes of S. pneumoniae of which twenty-three account for most of the disease. For a pneumococcal polysaccharide-protein conjugate to be successful, the capsular types responsible for most pneumococcal infections would have to be made adequately immunogenic. This approach may be difficult, because the twenty-three polysaccharides included in the presently-available vaccine are not all adequately immunogenic, even in adults. Furthermore, such a vaccine would probably be much more expensive to produce than any of the other childhood vaccines in routine use.

An alternative approach for protecting children, and also the elderly, from pneumococcal infection would be to identify protein antigens that could elicit protective immune responses. Such proteins may serve as a vaccine by themselves, may be used in conjunction with successful polysaccharide-protein conjugates, or as carriers for polysaccharides.

In McDaniel et al (I), J. Exp. Med. 160:386–397, 1984, there is described the production of hybridoma antibodies that recognize cell surface proteins on S. pneumoniae and protection of mice from infection with certain strains of encapsulated pneumococci by such antibodies. This surface protein antigen has been termed "pneumococcal surface protein A" or PspA for short.

In McDaniel et al (II), Microbial Pathogeniesis 1:519–531, 1986, there are described studies on the characterization of the PspA. From the results of McDaniel (II), McDaniel (III), J. Exp. Med. 165:381–394, 1987, Waltman et al., Microb. Pathog. 8:61–69, 1990 and Crain et al., Infect. Immun. 58:3293–3299, 1990, it was also apparent that the PspAs of different strains frequently exhibit considerable diversity in terms of their epitopes, and apparent molecular weight.

In McDaniel et al (III), there is disclosed that immunization of X-linked immunodeficient (XID) mice with non-encapsulated pneumococci expressing PspA, but not isogenic pneumococci lacking PspA, protects mice from subsequent fatal infection with pneumococci.

In McDaniel et al (IV), Infect. Immun., 59:222–228, 1991, there is described immunization of mice with a recombinant full length fragment of PspA that is able to elicit protection against pneumococcal strains of capsular types 6A and 3.

In Crain et al, (supra) there is described a rabbit antiserum that detects PspA in 100% (n=95) of clinical and laboratory isolates of strains of S. pneumoniae. When reacted with seven monoclonal antibodies to PspA, fifty-seven S. pneumoniae isolates exhibited thirty-one different patterns of reactivity. Accordingly, although a large number of serologically-different PspAs exist, there are extensive cross-reactions between PspAs.

The PspA protein type is independent of capsular type. It would seem that genetic mutation or exchange in the environment has allowed for the development of a large pool of strains which are highly diverse with respect to capsule, PspA, and possibly other molecules with variable structures. Variability of PspA's from different strains also is evident in their molecular weights, which range from 67 to 99 kD. The observed differences are stably inherited and are not the result of protein degradation.

Immunization with a partially purified PspA from a recombinant λ gt11 clone, elicited protection against challenge with several S. pneumoniae strains representing different capsular and PspA types, as described in McDaniel et al (IV), Infect. Immun. 59:222–228, 1991. Although clones expressing PspA were constructed according to that paper, the product was unstable and isolation from cell fragments following lysis was not effected.

While the protein is variable in structure between different pneumococcal strains, numerous cross-reactions exist between all PspA's, suggesting that sufficient common epitopes may be present to allow a single PspA or at least a small number of PspA's to elicit protection against a large number of S. pneumoniae strains.

In addition to the published literature specifically referred to above, the inventors, in conjunction with co-workers, have published further details concerning PspA's, as follows:

1. Abstracts of 89th Annual Meeting of the American Society for Microbiology, p. 125, item D-257, May 2989;

2. Abstracts of 90th Annual Meeting of the American Society for Microbiology, p. 98, item D-106, May 1990;

3. Abstracts of 3rd International ASM Conference on Streptococcal Genetics, p. 11, item 12, June 1990;

4. Talkington et al, Infect. Immun. 59:1285–1289, 1991;

5. Yother et al (I), J. Bacteriol. 174:601–609, 1992;

6. Yother et al (II), J. Bacteriol. 174:610–618, 1992; and

7. McDaniel et al (V), Microbiol Pathogenesis, 13:261–268.

In the aforementioned copending U.S. patent applications Ser. Nos. 656,773 and 835,698 (corresponding to published International patent application, WO 52/1448), as well as in Yother et al (I) and (II), there are described the preparation of mutants of S. pneumomiae that secrete an immunogenic truncated form of the PspA protein, and the isolation and purification of the secreted protein. The truncated form of PspA was found to be immunoprotective and to contain the protective epitopes of PspA. The PspA protein described therein is soluble in physiologic solution and lacks at least the functional cell membrane anchor region.

In the specification which follows and the drawings accompanying the same, there are utilized certain accepted abbreviations with respect to the amino acids represented thereby. The following Table I identifies those abbreviations:

TABLE I

AMINO ACID ABBREVIATIONS

| A | = | Ala | = | Alanine       | M | = | Met | = | Methionine  |
|---|---|-----|---|---------------|---|---|-----|---|-------------|
| C | = | Cys | = | Cysteine      | N | = | Asn | = | Asparagine  |
| D | = | Asp | = | Aspartic Acid | P | = | Pro | = | Proline     |
| E | = | Glu | = | Glutamic Acid | Q | = | Gln | = | Glutamine   |
| F | = | Phe | = | Phenylalanine | R | = | Arg | = | Arginine    |
| G | = | Gly | = | Glycine       | S | = | Ser | = | Serine      |
| H | = | His | = | Histidine     | T | = | Thr | = | Threonine   |
| I | = | Ile | = | Isoleucine    | V | = | Val | = | Valine      |
| K | = | Lys | = | Lysine        | W | = | Try | = | Tryptophan  |
| L | = | Leu | = | Leucine       | Y | = | Tyr | = | Tyrosine    |

SUMMARY OF INVENTION

In accordance with the present invention, there has been identified a 68-amino acid region of PspA from the Rx1 strain of *Streptococcus pneumoniae* which not only contains protection-eliciting epitopes, but also is sufficiently cross-reactive with other PspA's from other *S. pneumoniae* strains so as to be a suitable candidate for the region of PspA to be incorporated into a recombinant PspA vaccine.

The 68-amino acid sequence extends from amino acid residues 192 to 260 of the Rx1 PspA protein. While the disclosure herein refers specifically to the specific 68 amino acid sequence of the Rx1 PspA protein, any region of a PspA protein from any other *S. pneumoniae* species which is effectively homologous to this sequence of the Rx1 PspA protein is included within the scope of the invention, for example, from strains D39 and R36A.

Accordingly, in one aspect, the present invention provides an isolated PspA protein fragment comprising amino acid residues 192 to 260 of the PspA protein of the Rx1 strain of *Streptococcus pneumoniae* and containing at least one protection-eliciting epitope, and optionally up to a further 25 residues of the protein in the NH$_2$-terminal directional and/or the COOH-terminal direction, or being effectively homologous to such a fragment.

The protein fragment may be one containing an amino acid sequence corresponding to or effectively homologous to the amino acid residues 192 to 260 of the PspA protein of the Rx1 strain and hence may comprise fragments larger or smaller than ones containing the specific amino acid sequence.

The protein fragment of the invention may be produced recombinantly in the form of a truncated C-terminal deleted product containing the protein fragment, specifically a truncated C-terminal-deleted product containing the approximately C-terminal third of an α-helical region of the native PspA protein.

The present invention also includes an isolated protein fragment comprising an amino acid sequence corresponding to that of a protein-eliciting epitope contained in amino acid residues 192 to 260 of the PspA protein of the Rx1 strain of *Streptococcus pneumoniae*.

The amino acid sequence of the protein fragment need not be that found in strain Rx1 but can be based on a corresponding sequence from another strain. Thus, the present invention also includes an isolated protein fragment comprising an amino acid sequence corresponding to that of a protein-eliciting epitope contained in amino acid residues 192 to 260 of the PspA protein of the Rx1 strain of *Streptococcus pneumoniae*.

In particular, the invention includes an isolated protein fragment comprising the amino acid sequence of or effectively homologous with that of a protection-eliciting epitope corresponding to an epitope contained in amino acid residues 192 to 260 of the pneumococcal surface protein A (PspA) protein of the Rx1 strain of *Streptococcus pneumoniae*, and including no more than 25 additional amino acid residues in the NH$_2$— and/or the COOH-terminal direction.

We have further found that a PspA fragment including C-terminal regions of the PspA also contains protection-eliciting epitopes. Accordingly, in a further aspect, the present invention provides an isolated pneumococcal surface protein A (PspA) protein fragment comprising a C-terminal portion of the PspA protein from amino acid residue 192 up to and including the amino acid residue 588 of the Rx1 strain of *Streptococcus pneumoniae* are containing at least one protection-eliciting epitope and optionally up to a further 25 residues of the protein in the NH$_2$-terminal direction, or being effectively homologous with such a protein fragment.

Further, an additional aspect of the present invention provides an isolated protein fragment comprising the amino acid sequence of or effectively homologous with that of at least one protection-eliciting epitope corresponding to an epitope contained in a C-terminal portion of the pneumococcal surface protein A (PspA) protein from amino acid residue 192 up to and including amino acid residue 588 of the Rx1 strain of *Streptococcus pneumoniae*, and including no more than 25 additional amino acid residues in the NH$_2$-terminal direction.

We have further found that a PspA fragment including C-terminal regions of the PspA also contains protection-eliciting epitopes. Accordingly, in a further aspect, the present invention provides an isolated pneumococcal surface protein A (PspA) protein fragment comprising a C-terminal portion of the PspA protein from amino acid residue 192 up to and including the amino acid residue 588 of the Rx1 strain of *Streptococcus pneumoniae* are containing at least one protection-eliciting epitope and optionally up to a further 25 residues of the protein in the NH$_2$-terminal direction, or being effectively homologous with such a protein fragment.

Further, an additional aspect of the present invention provides an isolated protein fragment comprising the amino acid sequence of or effectively homologous with that of at least one protection-eliciting epitope corresponding to an epitope contained in a C-terminal portion of the pneumococcal surface protein A (PspA) protein from amino acid residue 192 up to and including amino acid residue 588 of the Rx1 strain of *Streptococcus pneumoniae*, and including no more than 25 additional amino acid residues in the NH$_2$-terminal direction.

In addition, we have found that the Pspa fragments provided herein, as used full-length PspA and other protection-eliciting epitope containing PspA fragments may be administered mucosally to a host to provide protection against diseases caused by pneumococcal infection.

Accordingly, in an additional aspect, the present invention provides a pneumococcal surface protein A (PspA) protein fragment comprising a plurality of conjugated molecules, each molecule comprising an isolated protein fragment corresponding to or effectively homologous with at least one protection-eliciting epitope corresponding to an epitope located in residues 192 to 260 of the PspA of strain Rx1, each molecule within the plurality being derived from different strains of S. pneumoniae.

The invention includes a vaccine or other immunogenic composition containing a protein fragment of the invention. It also includes certain DNA primers or probes and other biological materials as described herein.

BRIEF DESCRIPTION OF DRAWINGS

FIG. 1A–1C contains the DNA sequence for the pspA gene of the Rx1 strain of S. pneumoniae with the deduced amino acid sequence for the PspA protein;

GENERAL DESCRIPTION OF INVENTION

Figure 1A:
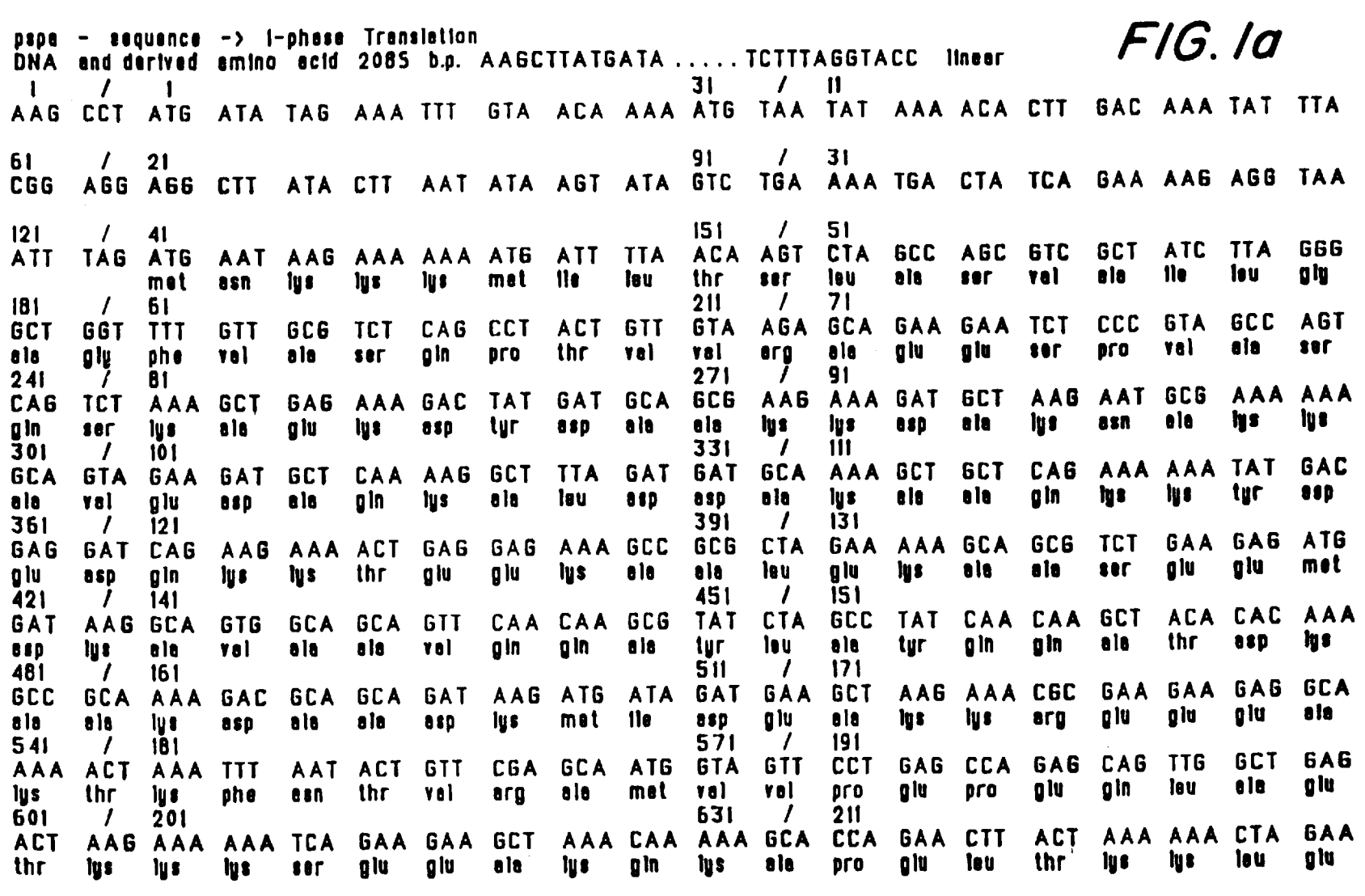
Figure 2:
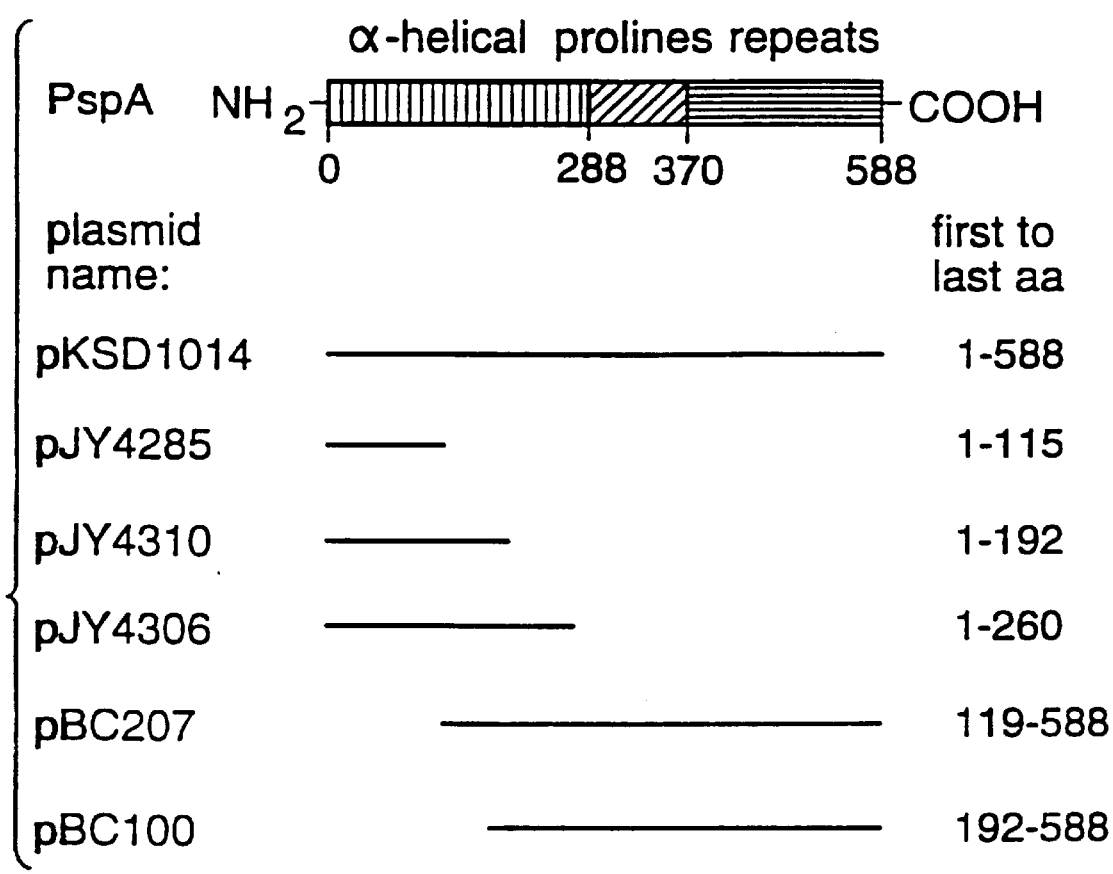
FIG. 2 contains a schematic representation of the domains of mature PspA protein as well as identification of certain plasmids containing gene sequences coding for the full length protein (pKSD 1014), coding for specific segments of the N-terminal portion of the protein (pJY4284 or pJY4285, pJY4310, pJY4306) and coding for specific sequences of the C-terminal region of the protein (pBC207, pBC100)

As described in the prior U.S. patent applications referred to above (and in corresponding WO 92/1448) and in Yother et al (I) and (II), the pspA gene of strain Rx1 encodes a 65 kDa molecule composed of 588 amino acids. The nucleotide sequence (SEQ ID No: 1) of the pspA gene and derived amino acid sequence (SEQ ID No: 2) are set forth in FIG. 1. The N-terminal half of the molecule is highly charged and its DNA sequence predicts an α-helical coiled-coil protein structure for this region (288 amino acids), as seen in FIG. 2. The C-terminal half of PspA, which is not α-helical, includes a proline-rich region (83 amino acids) and a repeat region containing the highly conserved twenty amino acid repeats, as well as a slightly hydrophobic sequence of 17 amino acids at the C-terminus. It is known that PspA is anchored to S. pneumoniae by its C-terminal half and it is likely that the proline-rich region serves to tangle the molecule in the cell wall. In addition, it is anticipated that the highly-charged α-helical region begins at the cell wall and extends into and possibly through the capsule. This model is supported by the observation that the α-helical domain contains all the surface exposed epitopes recognized by monoclonal antibodies (MAbs) reactive with PspA on the pneumococcal surfaces.

The PspA protein of S. pneumoniae strain Rx1 has been mapped to locate protection-eliciting epitopes. Such mapping has been effected by employing antibodies to PspA protein and recombinant fragments of PspA. This mapping technique, described in detail in the Examples below, has identified an amino acid sequence corresponding to the C-terminal third of the α-helical region of PspA as containing protection-eliciting epitopes, specifically the amino acid residues 192 to 260 of the Rx1 PspA protein. The amino acid sequence from residues 192 to 260 is the C-terminal third of the α-helical sequence, expected to be near the cell wall surface.

We have shown that a recombinant PspA fragment from Rx1 consisting of amino acids 192 to 260 (BAR 416) elicits cross-protection against challenge by a number of different wild-type strains of S. pneumoniae. In addition, recombinant PspA fragments from Rx1 expressed from E. coli by pBC100 and consisting of amino acids 192 to 588, i.e. including the C-terminal anchor region, also elicited cross-protection against challenge by a number of wild-type strains of S. pneumoniae, showing the presence of protection-eliciting epitopes.

Since the portion of the sequence from residues 192 to 260 contains only 68 amino acids, individual PspA protein fragments of this size may not be optimally antigenic. This difficulty is overcome by producing recombinant proteins containing tandem fragments of different PspAs expressed by gene fusions of the appropriate portions of several pspA genes.

Accordingly, in a further aspect of the invention, there is provided a PspA protein fragment comprising a plurality of conjugated molecules, each molecule comprising amino acid residues 192 to 260 of the PspA protein of the Rx1 strain of Streptococcus pneumoniae and containing at least one protection-eliciting epitope, each molecule being derived from a different strain of S. pneumoniae.

Such tandem molecules can be engineered to maintain proper coiled-coil structure at the points of junction and to be large enough to be immunogenic and to express an array of protection-eliciting epitopes that may cross-react with a wide spectrum of PspAs. Alternatively, individual recombinantly-produced peptides may be attached by chemical means to form a complex molecule.

A further alternative is to attach the PspA fragment to a larger carrier protein or bacterial cell, either as a recombinant fusion product or through chemical attachment, such as by covalent or ionic attachment.

The protein fragments, as well as peptide analogs thereof, provided herein are useful components of a vaccine against disease caused by pneumococcal infection. Accordingly, the present invention provides, in a yet further aspect, a vaccine comprising at least one PspA protein fragment as defined herein as an immunologically-active component thereof.

We have previously shown that, although PspAs are serologically variable, antisera raised against individual PspAs are sufficiently cross-reactive that they can frequently protect against pneumoniae which express serologically distinguishable PspAs. We have now shown that full-length PspAs from different pneumococcal strains, both from natural sources and produced recombinantly, can protect an animal model from challenge by different pneumococcal isolates. These results indicate that a limited number of serological PspA types may elicit protection against a broad spectrum of different pneumococci.

We have also demonstrated that protection can be elicited by mucosal administration, particularly intranasally, of PspA and immunogenic fragments thereof. The PspA or fragment thereof for such administration may be provided as a vaccine or other immunogenic composition comprising the PspA or fragment thereof and a physiologically-acceptable carrier therefor.

The immunogenic compositions, including vaccines, provided herein, comprising full-length PspA or the various PspA fragments described herein, elicit an immune response by the host to which it is administered including the production of antibodies by the host.

The immunogenic composition may be prepared as injectables, as liquid solutions or emulsions. The PspA or immunogenic fragment thereof may be mixed with physiologically acceptable carriers which are compatible with the PspA material. These carriers may include water, saline, dextrose, glycerol, ethanol and combinations thereof. The vaccine may further contain auxiliary substances, such as wetting or emulsifying agents, pH buffering agents, or adjuvants to further enhance the effectiveness of the vaccine. Vaccines may be administered by injection subcutaneously or intramuscularly.

Alternatively, and in a preferred embodiment as described above, the immunogenic compositions comprising full-length PspA or immunogenic fragments thereof formed according to the present invention, may be delivered in a manner to evoke an immune response at mucosal surfaces. Thus, the immunogenic composition may be administered to mucosal surfaces by, for example, the nasal or oral (intragastric) routes. Alternatively, other modes of administration including suppositories may be desirable. For suppositories, binders and carriers may include, for example, polyalkylene glycols and triglycerides. oral formulations may include normally employed incipients, such as pharmaceutical grades of saccharine, cellulose and magnesium carbonate.

These immunogenic compositions may take the form of solutions, suspensions, tablets, pills, capsules, sustained release formulations or powders and contain 1 to 95% of the microparticles of the present invention.

The immunogenic compositions are administered in a manner compatible with the dosage formulation, and in such amount as to be therapeutically effective, protective and immunogenic. The quantity to be administered depends on the subject to be treated, including, for example, the capacity of the subject's immune system to synthesize antibodies, and if needed, to produce a cell-mediated immune response. Precise amounts of PspA and/or fragment thereof required to be administered depend on the judgement of the practitioner. However, suitable dosage ranges are readily determinable by one skilled in the art and may be of the order of micrograms to milligrams. Suitable regimes for initial administration and booster doses are also variable, but may include an initial administration followed by subsequent administrations. The dosage of the vaccine may also depend on the route of administration and will vary according to the size of the host.

Now that the region constituted by amino acid residues 192 to 260 and constituted by residues 192 to 588 in the PspA protein of the Rx1 strain have been identified, those skilled in the art will readily be able to produce, by recombinant techniques, protein fragments according to the invention. In particular, DNA probes may be tailed in known manner for use in a PCR reaction to amplify genomic DNA coding for a desired fragment, insert the amplified DNA into a suitable plasmid vector and utilise the vector in a known manner to express the protein in a suitable host, such as *E. coli,* adopting, for example, the methods taught in Examples 2 and 3 below.

The appropriate PspA fragments may be cloned and expressed and their truncated products expressed under the control of an appropriate promoter, e.g. a vector containing the *E. coli* lac promoter expressing the *E. coli* ompA and leader sequence to create an ompa::pspA fusion plasmid. Optionally, the sequence coding for the PspA fragment may be linked to a sequence coding for a further protein suitable for injection into humans. Such proteins may be those already used as vaccines, because they are known to elicit protective immune responses and/or known to function as strong immunologic carriers. Such proteins may include the partial or complete amino acid sequence of toxins, such as tetanus toxin, or outer acid sequence of toxins, such as tetanus toxin, or outer membrane proteins, such as that of group B subtype 2 *Neisseria meningitis.*

It is also possible to produce a fusion protein composed of the cross-reactive protection-eliciting regions of several different PspA molecules, as mentioned above. Such a fusion protein may be made large enough ($\geq 40,000$ molecular weight) to be highly immunogenic and as a single protein may elicit cross-protection to as many different pneumococci as possible. The combination of cross-protective 70 amino acid regions from 5 to 6 PspAs would be large enough to be highly immunogenic. Constructs expressing epitopes from more than one PspA are especially attractive since PspAs of pneumococci are known to differ serologically. Present evidence indicates that a widely protective vaccine will need to contain cross-reactive protection-eliciting epitopes from more than one different pneumococcus.

It is possible to design such a fusion protein so that it also carries a domain that would assist with isolation of the fusion product by including the choline binding region of PspA, or a ligand binding domain from other proteins, such as the maltose binding protein (encoded by malE) of *E. coli.* In the former case, the fusion protein may be isolated by adsorption to a choline Sepharose® column and elution using 2% choline chloride. In the latter case, adsorption is to a mannose-Sepharose column, followed by elution with a solution containing mannose.

In the construction of such a fusion protein containing tandem cross-reactive coiled-coil PspA regions, it is critical not only that the appropriate open reading frame of each down stream gene fragment be preserved at the junctions of the ligated gene fragments, but that the heptad motif of the coiled-coil amino acid sequence not be disrupted. One way to accomplish the latter is to construct the gene fusions so that they occur within naturally occurring non-coil-coiled regions found in the α-helidal domain of PspA. In Yother et al (I), such non-coiled-coil breaks were identified at amino acid positions 169 to 176, 199, 225, 254, 274 and 289. Fusions between two or more cross-protective regions (residues 192–260) at or near positions 170 or 199 at one end and at or near residues 274 or 289 at the other end, can be expected to be able to express the epitopes normally expressed within the coiled-coil regions.

In each case, the simplest way to prepare such constructs is by PCR amplification of the DNA used to construct the gene fusions. In this way, it is possible to prepare the relevant sequence with appropriate restriction sites. The design of gene fusions and the PCR primers used to produce the individual pspa fragments will be carried out so that the proper reading frame will be preserved in each fused gene fragment at the nucleotide level.

It is also possible to synthesize peptides according to the invention having the appropriate amino acid sequence by conventional peptide synthesis.

The term "effectively homologous" used herein means in relation to an amino acid sequence effectively homologous to a defined sequence, that the said amino acid sequence may not be identical to said defined sequence but may be at least 70 percent, more preferably 80 percent, still more preferably 90 percent identical, provided that the antigenic epitope or epitopes in said amino acid sequence have properties substantially the same as the corresponding epitopes in said defined sequence.

BIOLOGICAL MATERIALS

The Examples which follow as well as in the accompanying drawings, reference is made to certain plasmid materials containing whole or truncated pspA gene sequences. The following Table II provides a summary of such materials:

TABLE II

| Plasmid | Identification | Gene Product |
|---|---|---|
| pKSD1014 | whole gene | amino acids 1 to 588 |
| pJY4284 or pJY4285 | 5' terminal region | amino acids 1 to 115 |
| pJY4310 | 5'-terminal region | amino acids 1 to 192 |
| pJY4306 | 5'-terminal region | amino acids 1 to 260 |
| pBC207 | 5'-terminal region | amino acids 119 to 588 |
| pBC100 | 5'-terminal region | amino acids 192 to 588 |

TABLE XXX

Reactivities of MAbs with PspAs from *Streptococcus pneumoniae*

| Streptococcus pneumoniae | | | | Monoclonal Antibody (isotype) | | | | | | | |
|---|---|---|---|---|---|---|---|---|---|---|---|
| | | | | XiR1526 | XiR35 | XiR1224 | Xi126 | XiR16 | X164 | XiR1325 | XiR270 | XiR1323 |
| Strain | Capsule type | PspA type | Ref. # | (IgG2b) | (IgG2a) | (IgM) | (IgG2b) | (IgG2a) | (IgM) | (IgG2a) | (IgG1) | (IgM) |
| Rx1 | rough | 25 | 36 | ++ | ++ | ++ | ++ | ++ | ++ | ++ | ++ | ++ |
| ATCC101813 | 3 | 3 | 37 | − | − | − | ++ | − | ++ | ++ | ++ | ++ |
| EF10197 | 3 | 18 | 38 | − | − | − | − | − | − | −/+ | ++ | − |
| RG9739 | 4 | 26 | 38 | − | − | − | − | − | − | ++ | + | ++ |
| LB1905 | 4 | 23 | 38 | − | − | − | − | − | − | − | − | − |
| BG-5-8A | 6A | 0 | 38 | − | − | + | −/+ | − | − | − | + | + |
| BG9163 | 6B | 21 | 38 | − | − | − | − | − | − | − | + | − |
| LM100 | 22 | ND | + | − | − | − | −/+ | − | − | − | − | − |
| WU2 | 3 | 1 | 39 | − | − | − | ++ | − | ++ | ++ | ++ | ++ |
| Protection against WU2 | | | | − | − | − | + | − | + | + | + | + |

EXAMPLES

Example 1

This Example describes the bacterial strains, plasmids and hybridoma antibodies used herein.

*S. pneumoniae* strains, identified in Table III below, were grown in Todd Hewitt broth with 0.5% yeast extract at 37° C. or on blood agar plates containing 3% sheep blood in a candle jar. *E. coli* strain DH1 (Hanahan, J. Mol. Biol. 166:557) was grown in LB medium or minimal E medium. Plasmids included pUC18 (Gene 33:103), pJY4163 (Yother et al (II)), and pIN-III-ompA (EMBO J. 3:2437).

All antibody-secreting hybridoma lines were obtained by fusions with non-antibody-secreting myeloma cell line P3-X63-Ag.8.653 (J. Immunol. 123:1548). The specific antibodies employed are identified in Table III below. The anti-PspA hybridoma cell lines Xi64, Xi126 and XiR278 have previously been described in McDaniel et al (I) and Crain et al (supra). The remaining cell lines were prepared by immunizing CBA/N mice with recombinant D39 PspA expressed in λgtII by the technique described in McDaniel et al (I). The cell lines producing antibodies to PspA were all identified using an ELISA in which microtitration plates were coated with heat-killed (60° C., 30 mins) *S. pneumoniae* R36A or Rx1, which would select for those MAbs that react with surface exposed epitopes on PspA. The heavy chain isotypes of the MAbs were determined by developing the ELISA with affinity purified goat antibody specific for μ and γ heavy chains of IgM and IgG mouse immunoglobulin. The specificity of the MAbs for PspA was confirmed by immunoblot analysis.

All six newly-produced MAbs, identified in Table III as XiR 1526, XiR 35, XiR 1224, XiR 16, XiR 1325 and XiR 1323, detected a protein of the expected size (apparent molecular weight of 84 kDa) in an immunoblot of strains Rx1 and D39. No reactivity was observed for any of the MAbs in an immunoblot of strain WG44.1, a PspA⁻ variant of Rx1 (see McDaniel et al (III) and Yother et al (II)).

Example 2

This Example describes the provision of the pspA gene from pneumococcal strain Rx1 by polymerase chain reaction (PCR).

Figure 1B:
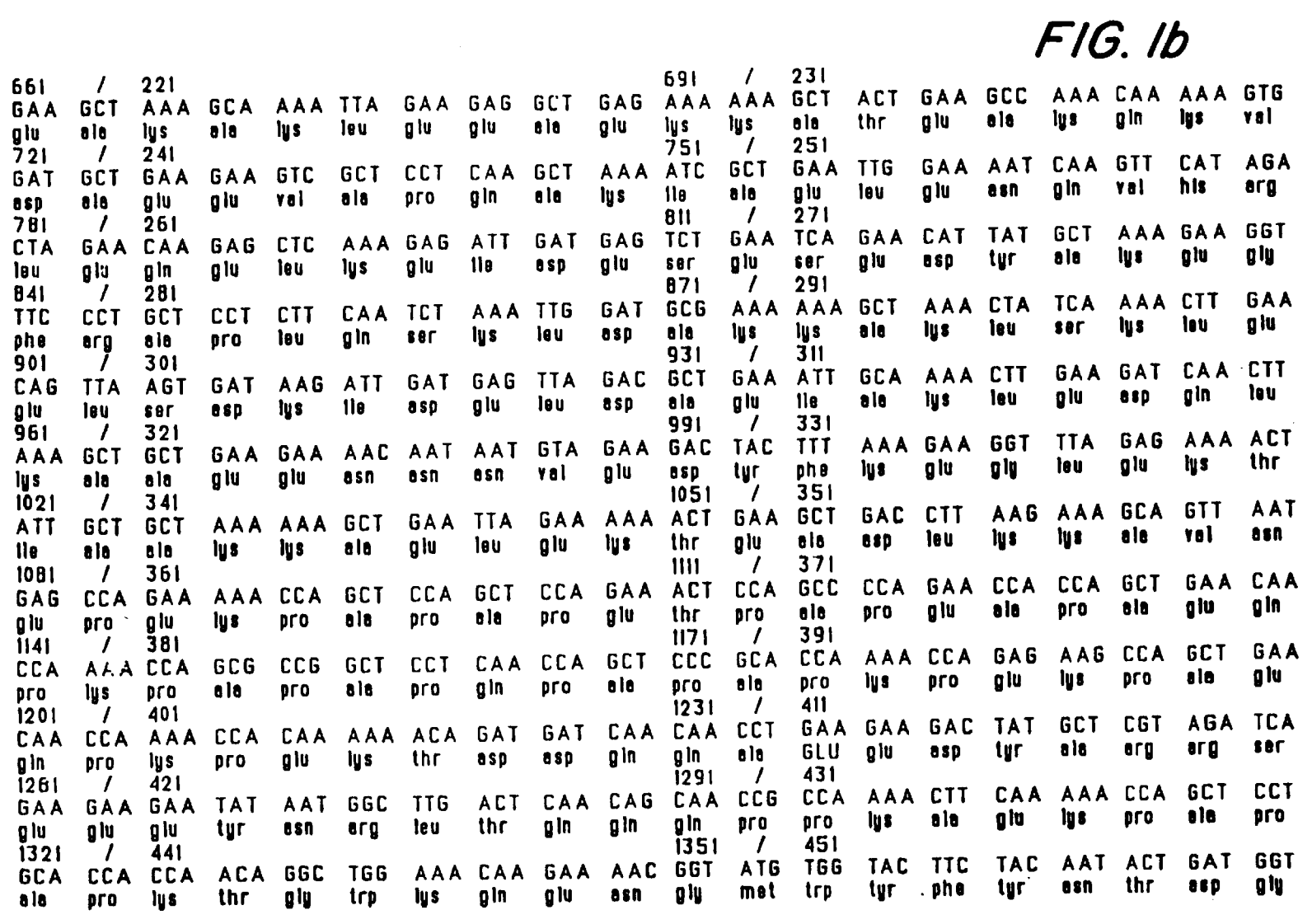
Figure 1C:
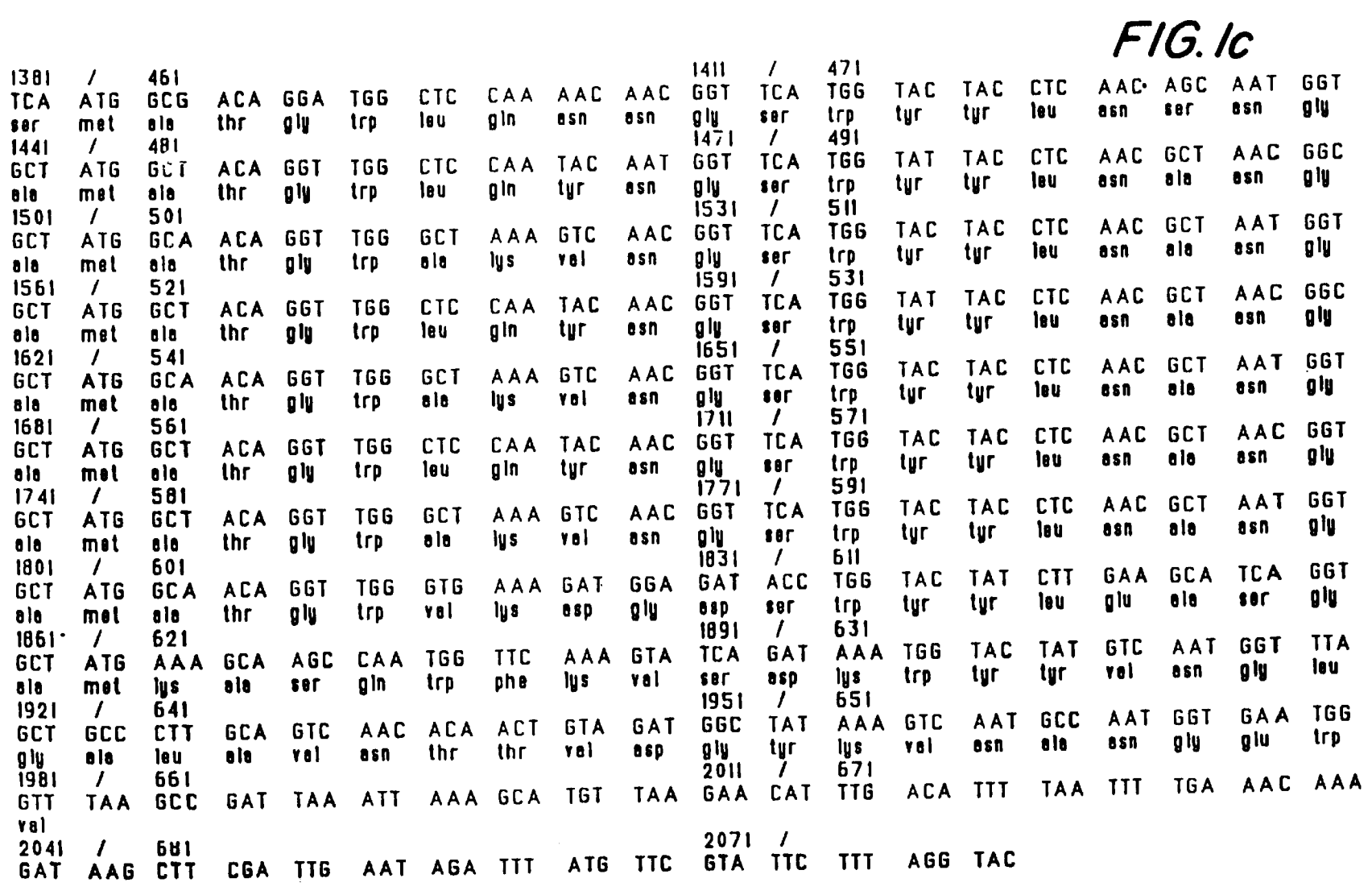

PCR primers were designed based on the sequence of the pspA gene from pneumococcal strain Rx1 (see FIG. 1). The 5'-primers were LSM3 and LSM4. LSM3 was 28 bases in length and started at base 576 and LSM4 was 31 bases in length and started at base 792, and both contained an additional BamHI site. The 3' pspA primer was LSM2 which was 33 bases in length and started at base 1990 and contained an additional SalI site.

The nucleotide sequences for the primers are as follows:
LSM2
5'-GCGCGTCGACGGCTTAAACCCATTCACCATTGG-3' (SEQ ID NO: 3)
LSM3 5'-CCGGATCCTGAGCCAGAGCAGTTGGCTG-3' (SEQ ID NO: 4)
LSM4
5'-CCGGATCCGCTCAAAGAGATTGATGAGTCTG-3' (SEQ ID NO: 5)

Approximately 10 ng of genomic Rx1 pneumococcal DNA was amplified using a 5' and 3' primer pair. The sample was brought to a total volume of 50 μl containing a final concentration of 50 mM KCl, 10 mM tris-HCl (pH 8.3), 1.5 mM MgCl$_2$, 0.001% gelatin, 0.5 mM each primer and 200 mM of each deoxynucleoside triphosphate and 2.5 U of Taq DNA polymerase. Following overlaying of the samples with 50 μl of mineral oil, the samples were denatured at 94° C. for 2 mins and then subjected to 10 cycles consisting of 1 min. at 94° C., 2 min. at 50° C. and 3 min. at 72° C., followed by another 20 cycles of 1 min. at 94° C., 2 min. at 60° C. and 3 min. at 72° C. After completion of the 30 cycles, the samples were held at 72° C. for an additional 5 min., prior to cooling to 4° C.

Example 3

This Example describes expression of truncated PspA molecules.

3'-deleted pspAs that express N-terminal fragments in *E. coli* and which secrete the same fragments from pneumococci were constructed as described in the aforementioned U.S. patent applications Ser. Nos. 835,698 and 656,773 (see also Yother et al (II), supra).

For expression of 5'-deleted pspA constructs, the secretion vector pIN-III-ompA was used. Amplified pspA fragments were digested with BamHI and SalI and ligated into the appropriately BamHI/SalI—digested pIN-III-ompA vector, providing the inserted fragment fused to the ompA leader sequence in frame and under control of the lac promoter. Transformants of *E. coli* DH1 were selected on minimal E medium supplemented with casamino acids (0.1%), glucose (0.2%) and thiamine (0.05 mM) with 50 μg/ml of ampicillin.

Figure 4:
FIG. 4 is an immunoblot of PspA protein gene products produced by plasmids identified therein.
Figure 4:
Figure 4:
Figure 4:

For induction of lac expression, bacteria were grown to an optical density of approximately 0.6 at 660 nm at 37° C. in minimal E medium and IPTG was added to a concentration of 2 mM. The cells were incubated for an additional two hours at 37° C. harvested and the periplasmic contents released by osmotic shock. An immunoblot of the truncated PspA proteins produced by the various plasmids is shown in FIG. 4.

By these procedures, there were provided, for the 3'-deleted pspAs, plasmids pJY4284, pJY4285, pJY4310 and pJY4306 and for the 5'-deleted pspAs, plasmids pBC207 and pBC100. Plasmid pJY4284 and pJY4285 contain an insert of 564 base pairs, nucleotides 1 to 564 and encoded a predicted 13 kDa PspA C-terminal-deleted product corresponding to amino acids 1 to 115. Plasmid pJY4310 contains an insert of 795 base pairs, nucleotides 1 to 795 and encoded a predicted 21 kDa C-terminal-deleted product corresponding to amino acid 1 to 192. However pJY4306 contained an insert of 999 base pairs, nucleotides 1 to 999 and encoded a predicted 29 kDa C-terminal-deleted product corresponding to amino acids 1 to 260. Plasmid pBC100 contained an insert of 1199 base pairs, nucleotides 792 to 1990, and encoded a predicted 44 kDa PspA N-terminal deleted product contained amino acids 192 to 588. pBC207 contained an insert of 1415 base pairs, nucleotide 576 to 1990, and encoded a predicted 52 kDa PspA N-terminal deleted product containing amino acids 119 to 588.

The pspA gene sequences contained in these plasmids code for and express amino acids as identified in FIG. 2. A plasmid also was prepared by these techniques encoding a PspA containing amino acids 192 to 260.

Example 4

This Example describes the procedure of effecting immunoassays.

Immunoblot analysis was carried out as described in McDaniel et al (IV). The truncated PspA modules prepared as described in Example 3 or pneumococcal preparations enriched for PspA (as described in McDaniel et al (II)) were electrophoresed in a 10% sodium dodecyl sulfate polyacrylamide gel and electroblotted onto nitrocelluloses. The blots were probed with individual MAbs, prepared as described in Example 1.

A direct binding ELISA procedure was used to quantitatively confirm reactivities observed by immunoblotting. In this procedure, osmotic shock preparations were diluted to a total protein concentration of 3 μg/ml in phosphate buffered saline (PBS) and 100 μl was added to wells of Immulon 4 microtitration plates. After blocking with 1% bovine serum albumin in PBS, unfractionated tissue culture supernates of individual MAbs were titered in duplicate by 3-fold serial dilution through 7 wells and developed as described in McDaniel et al (IV) using a goat anti-mouse immunoglobulin alkaline phosphate conjugated secondary antibody and alkaline phosphate substrate. Plates were read in a Dynatech plate reader at 405 nm, and the 30% end point was calculated for each antibody with each preparation.

The protective capacity of the MAbs was tested by injecting three CBA/N mice i.p. with 0.1 ml of ⅒ dilution (about 5 to 30 μg) of each hybridoma antibody 1 hr prior to i.v. injection of $10^3$ CFU of WU2 or D39 pneumococci (>100×$LD_{50}$). Protection was judged as the ability to prevent death of all mice in a group. All non-protected mice died of pneumococcal infection within 48 hours post challenge.

Example 5

This Example describes mapping of the epitopes on PspA using the monoclonal antibodies described in Example 1.

The six newly-produced monoclonal antibodies described in Example 1 and identified in Table III were used along with the previously-described monoclonal antibodies X164, Xi126 and XiR278 to map epitopes on PspA.

To determine whether each of the MAbs recognized different epitopes, each of them was reacted with eight additional *S. pneumoniae* strains, as identified in Table III, in immunoblots of SDS-PAGE separated proteins. Seven different patterns of activity were observed. Three antibodies, XiR16, XiR35 and XiR1526, appeared to recognize epitopes found on Rx1 PspA but none of the other PspAs. Accordingly, it was possible that these three antibodies might all react with the same epitope as Rx1 PspA.

MAb Xi64 and Xi126 both reacted strongly only with epitopes on ATCC 101813, WU2 and Rx1 PspAs, but not with PspAs of the other strains. However, it is known from studies of larger panels of PspAs (as described in McDaniel et al (III) and Crain et al) that Xi126 and Xi64 recognize different determinates.

The remaining four antibodies each exhibited unique patterns of reactivity with the panel of PspAs. Accordingly, the nine antibodies tested recognized at least seven different epitopes on PspA.

For reasons which are not clear, the type 2 strain D39 appeared to be uniquely able to resist the protective effects of antibodies to PspA (McDaniel et al (IV)). As described in McDaniel et al (I), greater than forty times the amount of Xi126 was required to passively protect against the D39 strain as compared to the WU2 strain. None of the six newly-produced monoclonal antibodies protected against the D39 strain. In contrast, immunization of mice with Rx1 PspA elicits protection against A66, WU2 and EF6796 strains (mouse virulent pneumococci of capsular types 3, 3 and 6A respectively), all of which have PspA types that are different from those of Rx1 and D39 (see McDaniel et al (IV)). In view of the close serologic similarity between the type 25 PspA of Rx1 and type 1 PspA of Wu2 (Crain et al), WU2 pneumococci were used to challenge mice that had been passively protected with the MAbs. All five of the MAbs that were observed to bind WU2 PspA were able to protect against infection with 1000 CFU of WU2. Protective antibodies were found in IgM, IgG1, IgG2b and Ig2a heavy chain isotype classes.

Example 6

This Example describes mapping of the epitopes of PspA using the recombinant truncated PspA molecules formed in Example 3.

The five-overlapping C-terminal or N-terminal deleted PspA fragments, prepared as described in Example 3 and shown in FIG. 2, were used to map epitopes on PspA. The general location of the epitopes detected by each of the mice MAbs, as described in Example 5, was determined using the five C-terminal-deleted and two N-terminal deleted PspA molecules. As a positive control, the reactivity of each antibody was examined with a clone, pKSD1014, expressing full-length PspA.

As noted earlier, the reactivity of the MAb was determined by two methods. In one method, reactivity between the fragments and MAb was evaluated in immunoblots of the fragment preparations after they had been separated by SDS-PAGE. In the second method, a direct ELISA was used to quantify the reactivity of the MAbs with non-denatured PspA fragment.

The reactivities observed and the quantification of such activity is set forth in the following Table IV:

fragment and both of the N-terminal-deleted fragments, thus locating their determinants between amino acid positions 192 and 260. Generally confirmatory results were obtained in ELISAs with the native molecules. However, in a few cases, reactions were observed in ELISAs with full length PspA but not with a truncated molecule even though the same truncated fragment was reactive with the antibody by immunoblot. These observations may have resulted from an altered conformation of the truncated fragments under physiologic conditions that masked or prevented the formation of determinant present in full-length PspA and in the denatured fragments.

Two antibodies XiR216 and XiR1323 showed what, at first appeared to be anomalous reactions, indicating that epitopes detected by the antibodies might be in more than one portion of PspA. In view of this unexpected result, the assays were repeated multiple times with two sets of preparations of the truncated fragments. The results of the additional assays confirmed the two-position mapping of epitopes for these two MAbs.

By immunoblot, MAb XiR16 reacted strongly with the two longest C-terminal-deleted fragments and failed to react with the shortest N-terminal-deleted fragment. Accordingly, the epitope detected must be N-terminal to position 192. Unexpectedly, MAb XiR16 reacted weakly in immunoblots with both the longest N-terminal-deleted fragment (residues 119 to 158) and the shortest C-terminal-deleted fragment

TABLE IV

Reactivity of PspA Fragments with Monoclonal Antibodies[1]

| PspA Fragments | Xi126 | | XiR35 | | XiR1526 | | XiR1224 | | XiR16 | | XiR1323 | | Xi64 | | XiR1325 | | XiR278 | |
|---|---|---|---|---|---|---|---|---|---|---|---|---|---|---|---|---|---|---|
| pJY4285 | ++ | 72 | ++ | 5 | ++ | <3 | + | <3 | + | 4 | – | <3 | – | <3 | – | <3 | – | <3 |
| pJY4310 | ++ | 116 | ++ | 4 | ++ | <3 | + | 5 | ++ | 16 | – | 31 | – | <3 | – | <3 | – | <3 |
| pJY4306 | ++ | 1127 | ++ | 78 | ++ | 554 | ++ | 805 | ++ | 2614 | ++ | <3 | ++ | 643 | ++ | 717 | + | <3 |
| pBC207 | – | <3 | – | <3 | – | <3 | – | <3 | + | <3 | ++ | 61 | ++ | <3 | ++ | <3 | ++ | 4527 |
| pBC100 | – | <3 | – | <3 | – | <3 | – | <3 | – | <3 | ++ | 15 | ++ | 709 | ++ | 4401 | ++ | 4746 |
| Rx1 | ++ | 63 | ++ | 15 | ++ | 42 | ++ | 48 | ++ | 118 | ++ | 44 | ++ | 64 | ++ | 111 | ++ | 468 |
| pIN-111 | – | <3 | – | <3 | – | <3 | – | <3 | – | <3 | – | <3 | – | <3 | – | <3 | – | <3 |

1. Antibodies were reacted with the indicated PspA fragments in immunobin: of SDS-PAGE separations, or by ELISA using microtitration plates coated with preparations enriched for the indicated PspA fragments. Rxl PspA serves as a positive control, and pIN-111-ompA (vector alone) serves as a negative control. The results of the immunoblot are presented as ++ (strong reaction), + (weak but clearly positive reaction) and – (no reaction). ELISA values are given as the reciprocal dilution of each monoclonal antibody that gave 30% of maximum binding with wells coted with the indicate fragment preparation.
The asterisk (*) after some of the antibodies denotes those which are able to protect against fatal pneumococcal infection wth strain WU2 or D39 *S. pneumonaie*.

Figure 3:
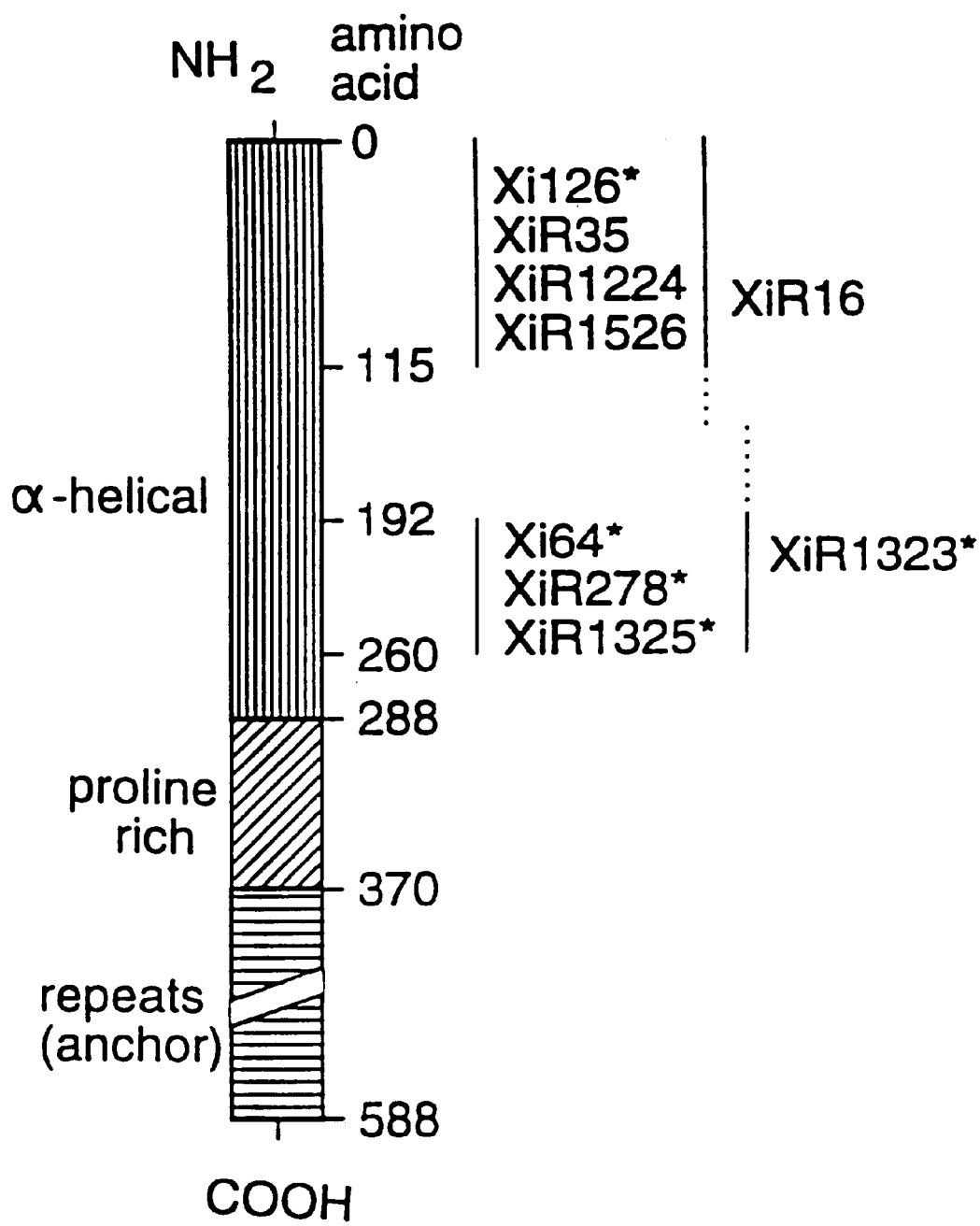
FIG. 3 contains a schematic representation of the domains of the mature PspA protein and the general location of epitopes recognized by certain monoclonal antibodies.

The deduced locations of the epitopes are indicated in FIG. 3.

As can be seen from the data in Table IV, three of the antibodies, Xi126 and XiR35 and XiR1526, react strongly with all three C-terminal-deleted clones in immunoblot analysis, indicating that the sequence required to form the epitope(s) detected by all three lies within the first 115 amino acids of PspA. This map position is in agreement with the failure of these antibodies to react with either of the N-terminal-deleted clones that lack the first 119 and 191 amino acids.

MAb XiR1224 reacted strongly by immunoblot with the longest C-terminal-deleted fragment (pJY4306), but showed substantially weaker reactions with the shorter two C-terminal-deleted fragments. This result indicates that, while the binding site of the antibody may be in the first 115 amino acids, residues beyond amino acid 192 may be important for the conformation or stability of the epitope.

By immunoblot, the three antibodies Xi64, XiR1325 and XiR278, all reacted with the longest C-terminal-deleted (residues 1 to 115). Since the fragments do not overlap, and if the weak immunoblot reactivities with fragments (reactivities not seen by ELISA) are not an artifact, the MAb XiR16 must recognize epitopes on both fragments.

In the case of MAb XiR1323, the immunoblot data clearly places the detected epitope between positions 192 and 260. In the ELISA studies, however, XiR1323 reacted strongly and reproducibly with the C-terminal-deleted fragment pJY4310 (amino acid residues 1 to 192) as well as the shortest N-terminal-deleted fragment pBC100 (amino acid residues 192 to 588). Curiously, an ELISA reaction was not observed between MAb XiR1323 and pJY4306 (amino acid residues 1 to 260), even though MAb XiR1323 reacted strongly with this fragment by immunoblot.

These findings provide additional evidence for distal conformation effects on antigenic determinants of PspA. They also indicate that, on the native fragments, MAb XiR1323 sees epitopes on both sides of position 192. The relationship between expression of the epitopes in other PspAs and their position in Rx1 PspA is demonstrated in Table IV in which is listed the antibodies in accordance with their apparent map position in PspA. The five antibodies (including XiR16) that clearly recognize epitopes N-terminal to position 116 are listed at the left side of Table IV. The four antibodies that clearly recognize epitopes C-terminal to position 192 are listed on the right side of Table IV. Three of the five epitopes N-terminal of position 192 (those recognized by XiR1526, XiR35, and XiR16) were not found on any of the other eight PspAs treated. One epitope (recognized by XiR 1224) was weakly expressed by one other strain and another (recognized by Xi126) was expressed on two other strains. In contrast, the four epitopes present in the C-terminal third of the PspA α-helical region were each present in form two to six other strains. The greater conservation of the region C-terminal to position 192, as compared to the region N-terminal to position 192 was significant at P<0.05 by both the Chi-square and the two sample rank tests. Based on the mapping results (Table III) and the strain distribution results (Table IV), it is apparent that all of the antibodies except possibly XiR35 and XiR1526 must recognize different PspA determinants.

Example 7

This Example contains a discussion of the mapping results achieved in Example 6.

The results set forth in Example 6 clearly demonstrate that the protection eliciting epitopes of PspA are not restricted to the N-terminal end of the surface exposed α-helical half of the molecule. In fact, four of the five antibodies protective against *S. pneumoniae* WU2 reacted with the C-terminal third of the α-helical region of PspA. This portion of the α-helical region is thought to closest to the cell wall (see Yother et al (II)).

About half of the MAbs recognized determinants N-terminal to amino acid 115 and the other half recognized epitopes C-terminal to residue 192. Since the nine antibodies were selected for their ability to bind native PspA on the surface of heat-killed whole pneumococci, the distribution of the epitopes they recognize suggests that determinants between positions 115 and 192 are either not immunogenic or are not exposed on the native molecule as expressed on pneumococci.

Curiously two MAbs (XiR16 and XiR1323) appeared to possibly react with epitopes in more than one position on PspA. Although the bulk of the data for XiR16 placed its epitope N-terminal of position 115, weak immunoblot patterns suggested that a reactive epitope(s) may also exist C-terminal to residue 115. In the case of XiR1323, the bulk of the data indicated that its epitope is between positions 192 and 260. However, the ELISA assay showed significant reactivity of the antibody with a C-terminal-deleted PspA fragment extending from residues 1 to 192. Although there are no extensive repeats in the N-terminal half of PspA, there are a few short repeated sequences that occur more than once in the coiled-coil motif. One such sequence is glu-glu-ala-lys which starts at amino acid positions 105, 133, and 147 and another is lys-ala-lys-leu starting at positions 150 and 220 (see FIG. 1). In the case of XiR1323, the antibody reacted with the epitope on the 1 to 192 fragment under natured but not denatured conditions. This may indicate that the epitope is conformational and may not have the same exact sequence as the epitope recognized (under both natured and denatured conditions) between residues 192 and 260.

One mechanism that may account for the lack of exposure of epitopes between amino acid 115 and 192 would be a folding back of this portion of the α-helical sequence on itself or other parts of PspA to form a coiled-coil structure more complex than a simple coiled-coil dimer. If this occurred, it could explain how PspA tertiary structure can sometimes be dependent on distant PspA structures. A suggestion that this might, in fact, be the case comes from the observation that some of the truncated forms did not express certain epitopes under physiologic conditions that were detected on the whole molecule under the same conditions and were shown to be present in the fragment after denaturation in SDS.

Since a PspA vaccine may need to contain fragments of several serologically different PspAs, it would be desirable to include in a vaccine only those portions of each PspA that are most likely to elicit cross-protective antibodies. Based on the results presented herein with Rx1 PspA, it appears likely that the portion of the PspA sequences corresponding to residues 192 to 260 of Rx1 PspA is the best portion of PspA to include in a recombinant PspA vaccine. The epitopes in this portion of PspA were three and a half times as likely to be present in the PspAs of other strains as the epitopes in the residue 1 to 115 portion of the sequence, and none of the 9 antibodies studied clearly reacted with the middle third of the α-helical region.

Example 8

This Example shows cross-protection of an animal model against challenge by a variety of virulent pneumococcal strains by recombinant PspA fragments.

Five mice were immunized with purified PspA fragment produced by pBC207 (produced as described in Example III) in *E. coli* and five with PspA purified fragment produced by pBC100 (produced as described in Example III) in *E. coli*. In both cases, the fragments were injected in Freund's Complete Adjuvant, boosted two weeks later with the fragment in saline and challenged 7 days post boost. All mice immunized with each fragment survived challenge with 100×LD$_{50}$ of WU2 capsular type 3 *S. pneumoniae*.

Five additional mice were injected with adjuvant plus an equivalent preparation of non-PspA producing *E. coli*. All mice died when challenged with the same dose of WU2 strain.

In addition, further numbers of mice were immunized with purified fragment produced by pBC100 in *E. coli* following the protocol described above. The mice were challenged with a variety of virulent strains and the pBC100 fragment was found to protect mice against 7 of 14 virulent strains and to extend life for the other 7 strains. The results obtained, which includes the result for the WU2 challenge, are set forth in the following Table V:

TABLE V

Protection Mediated by Recombinant (BC100) (amino acids 192–588) PspA from strain Rx1

| Challenge strain | Serotype | | Alive: Dead | | Median Day of Death | |
|---|---|---|---|---|---|---|
| | Caps | PspA | BC100 (rPspA) | none | BC100 (rPspA) | none |
| D39 | 2 | 25 | 0:5 | 0:3 | 5 | 2 |
| WU2 | 3 | 1 | 4:0 | 0:3 | >21* | 3 |
| A66 | 3 | 13 | 4:0 | 0:3 | >21* | 1 |
| EF10197 | 3 | 18 | 5:0 | 0:3 | >21* | 2 |

TABLE V-continued

Protection Mediated by Recombinant (BC100)
(amino acids 192–588) PspA from strain Rx1

| Challenge strain | Serotype Caps | PspA | Alive: Dead BC100 (rPspA) | none | Median Day of Death BC100 (rPspA) | none |
|---|---|---|---|---|---|---|
| ATCC6303 | 3 | 7 | 5:0 | 0:5 | >21** | 5 |
| EF5668 | 4 | 12 | 1:3 | 0:3 | 9.5 | 4 |
| EF3296 | 4 | 20 | 1:3 | 0:3 | 5 | 3 |
| L81905 | 4 | 23 | 1:5 | 0:6 | 5* | 2.5 |
| BC9739 | 4 | 26 | 0:4 | 0:3 | 7 | 2 |
| DBL5 | 5 | 33 | 0:5 | 0:3 | 5* | 2 |
| EG7322 | 6 | 24 | 4:0 | 1:3 | >21* | 6 |
| EF6796 | 6A | 1 | 4:0 | 0:3 | >21* | 1 |
| DBL6A | 6A | 19 | 5:0 | 0:3 | >21* | 7 |

*, different from "none" at P≦ .004 in one tailed tests,
**, different from "none" at P≦ .05 one tailed tests, all are Fisher exact except DBL5 and L81905 where the one tailed two sample rank test was used.

Further, additional mice were immunized with a purified PspA fragment (BAR 416) produced by *E. coli* and corresponding to amino acids 192 to 260, following the protocol described above and challenged with various strains of *S. pneumoniae* against which protection was provided by the pBC100-derived fragment. The results obtained are contained in the following Table VI:

TABLE VI

Protection Mediated by Recombinant (BAR416)
(amino acids 192–260) PspA from strain Rx1

| Challenge strain | Serotype Caps | PspA | Alive: Dead BAR416 (rPspA) | none | Median Day of Death BAR416 (rPspA) | none |
|---|---|---|---|---|---|---|
| WU2 | 3 | 1 | 4:1 | 0:4 | >21 | 3 |
| A66 | 3 | 13 | 5:0 | 0:5 | >21 | 2 |
| BG7322 | 6B | 24 | 3:2 | 0:4 | >21 | 7 |
| ATCC6303 | 3 | 7 | 5:0 | 0:5 | >21 | 5 |
| EF6796 | 6A | 1 | 3:2 | 0:5 | >21 | 5 |
| DBL6A | 6A | 19 | 5:0 | 0:5 | 7 | 2 |

The strains tested are all strains protected against by immunization with BC100. The results indicate that the region from 192–260 is able to elicit much of the cross-protection elicited by BC100.
Infected with ≧100 × LD$_{52}$ of each strain. In all cases this is ≧10$^3$ CFU.

As may be seen from this Table VI, protection was afforded against challenge in many instances and in others the life was extended.

The data presented in this Example conclusively proves that epitopes C-terminal to amino acids 119 and 192 respectively are capable of eliciting protective immunity. This result is consistent with the findings presented in the earlier Examples that the region of PspA from amino acids 192 to 260 contains at least one protection-eliciting epitope.

Example 9

This Example shows the cross-protection of an animal model against challenge by a variety of pneumococcal strains by whole-length recombinant PspA's.

Five mice were immunized with purified whole length recombinant PspAs from the Rx1 and EF5668 strains of *Streptococcus pneumoniae,* expressed in *E. coli.* The PspA was injected subcutaneously in Freund's complete adjuvant, boosted two weeks later with the whole length PspA in incomplete Freund's adjuvant, and challenged intravenously 7 days post boost, with 100×LD$_{50}$ of the virulent strain.

The results obtained are shown in the following Tables VII and VIII:

TABLE VII

Protection Against *Streptococcus pneumoniae* Isolates By Immunization with Rx1 or EF5668 PspA

| Challenge Strains | Serotype Capsule | PspA | Immunizing PspA (++ = protected + = extended life 0 = little effect) Rx1* PspA type 25 | EF5668 PspA type 12 | Best of Rx1 or EF5668 |
|---|---|---|---|---|---|
| WU2 | 3 | 1 | ++ | ++ | ++ |
| A66 | 3 | 13 | ++ | ++ | ++ |
| EF10197 | 3 | 18 | ++ | | ++ |
| ATCC6303 | 3 | 7 | ++ | | ++ |
| BG9739 | 4 | 26 | + | | + |
| EF3296 | 4 | 20 | +/0 | | +/0 |
| L81905 | 4 | 23 | + | | + |
| EF5668 | 4 | 12 | + | ++ | ++ |
| EF6796 | 6A | 1 | ++ | ++ | ++ |
| DBL6A | 6A | 19 | ++ | | ++ |
| GB9163 | 6B | 21 | ++ | | ++ |
| BG7322 | 6B | 24 | ++ | ++ | ++ |
| DBL5 | 5 | 33 | + | | + |
| D39 | 2 | 25 | ++/+/0$^a$ | + | ++/+/0$^a$ |
| Proportion of Strains Protected Against Fatal Infection | | | 57% | | 64% |

*The Rx1 data represents pooled results form immunization with full-length and fragments of Rx1 PspA.
$^a$Protection against death was observed but only with 10× more Ab than was required than for protection against WU2.

TABLE VIII

Protection Mediated by Recombinant full-length PspA from Strain EF5668

| Challenge strain | Serologic type Capsule | PspA | Alive:Dead (rPspA) | no PspA | Median Day of Death (rPspA) | no PspA | P value |
|---|---|---|---|---|---|---|---|
| WU2 | 3 | 1 | 8:0 | 0:7 | >10 | 2 | <0.001 |
| A66 | 3 | 13 | 4:1 | 0:4 | >10 | 2.5 | <0.05 |
| EF5668 | 4 | 12 | 5:0 | 1:4 | >10 | 2 | <0.01 |
| BG7322 | 6 | 24 | 5:1 | 1:5 | >10 | 7 | <0.025 |
| D39 | 2 | 25 | 3:2 | 0:5 | >10 | 3 | N.S. |

Challenge was with 1000 CFU in XID mice (in all cases ≧ 100X the LD$_{50}$).

As may be seen from the Tables VII and VIII, the PspA from Rx1 provided protection against a broad spectrum of *S. pneumoniae* strains while that from EF5668 also provided cross-protection against a number of strains. These results indicate that a limited number of serological PspA types may elicit protection against a broad spectrum of different pneumococci. This data also substantiates the potential use of PspA as an important component of a protein-based pneumococcal vaccine.

Example 10

This Example illustrates protection in an animal model against challenge by a virulent pneumococcal strain by mucosal administration of whole-length PspA.

Whole-length PspA was recovered from *S. pneumoniae* R36A strain (which provides the same PspA as the Rx1 strain). The strain (100 ml) was grown in chemically-defined medium (Rijn et al, Infect. & Immun. 1990, vol. 27, pp 444–448), except that the medium contained 0.03% choline chloride. The bacteria were harvested in late log phase (about $5 \times 10^7$ CFU/ml) and washed five times with 20 ml of saline followed by centrifugation at 2000 xg for 10 minutes. With each wash, the bacteria was saved and the supernatant discarded. The washed cells then were eluted with 5 ml of 2% choline chloride and the eluted material was shown to contain PspA by dot blot using monoclonal antibody XiR 278.

An identical procedure was carried out on the *S. pneumoniae* strain WG44.1 (McDaniel et al (III)), which does not produce PspA because of the absence of an up-stream portion of the pspA gene. This material provided a control in that the preparation should contain the same general impurities that might be in the extract from R36A. The material recovered from the washed WG44.1 cells by elution with 2% choline chloride did not contain detectable PspA by dot blot, as expected.

For the purpose of administration, the PspA preparation from R36A was diluted ½. 12 μl of the solution contained 5 μg of added cholera toxin B subunit (CTB) as an adjuvant and was instilled into the nose of each BALB/cJ mouse. Thirty-two and forty-two days later the immunization was repeated in an identical manner. As a control, some mice were immunized with an identical preparation from the WG44.1 *S. pneumoniae* strain. A final group was left unimmunized. Seven days after the third dose, the immunized mice were challenged with $2 \times 10^6$ CFU ($100 \times LD_{50}$) of A66 *S. pneumoniae* intratracheally.

Activity assays also were performed on sera obtained seven days after the third immunization on separate groups of mice immunized by protocols almost identical to those noted above.

The results obtained are set forth in the following Table IX:

TABLE IX

Intranasal Immunization with Rx1 PspA and Intratracheal Challenge with Capsular Type 3 Strain A66

| Immunogen | Adjuvant | IgG anti-PspA (μg/ml) | Challenge CFU of A66 | CFU/ml at day 3 | Day of Death |
|---|---|---|---|---|---|
| FL PspA (R36A) | CTB | | $2 \times 10^6$ | $<10^2$ | >12** |
| | " | 17.8 | " | $<10^2$ | >12 |
| | " | ±3.3 | " | $<10^2$ | >12 |
| | " | | " | $<10^2$ | >12 |
| PspA (WG44.1) | CTB | | $2 \times 10^6$ | $2 \times 10^5$ | 3 |
| | " | ≤0.4 | " | $4 \times 10^5$ | 4 |
| | " | | " | $4 \times 10^4$ | 4 |
| | " | | " | $2 \times 10^4$ | 4 |
| Saline | Saline | | $2 \times 10^6$ | N.D. | 4 |
| " | " | ≤0.4 | " | N.D. | 4 |
| " | " | | $2 \times 10^5$ | N.D. | 4 |
| " | " | | " | N.D. | 5 |

**FL-PspA vs. Saline (or WG44.1) at P<.005

As may be seen from this Table IX, a significant degree of protection was afforded by the intranasal administration of full-length PspA.

| SEQUENCE IDENTIFICATIONS | |
|---|---|
| SEQ ID NO: 1 | DNA sequence for psPA gene (Figure 1) |
| SEQ ID NO: 2 | Deduced amino acid sequence for PspA protein (Figure 1) |
| SEQ ID NO: 3 | Nucleotide sequence for PCR primer LSM 2 |
| SEQ ID NO: 4 | Nucleotide sequence for PCR primer LSM 3 |
| SEQ ID NO: 5 | Nucleotide sequence for PCR primer LSM 4 |

SUMMARY OF THE DISCLOSURE

In summary of this disclosure, the present invention provides PspA protein fragments which contain protection-eliciting epitopes and which are cross-reactive and can be incorporated into a vaccine against disease caused by pneumococcal infection. Modifications are possible within the scope of this invention.

What we claim is:

1. An isolated, truncated pneumococcal surface protein A (PspA) fragment comprising amino acid residues 192 to 588 or 167 to 588 of PspA of *Streptococcus pneumoniae* and containing at least one protection-eliciting epitope.

2. The fragment of claim 1 containing an amino acid sequence corresponding to amino acid.

3. An isolated polypeptide comprising at least one protection-eliciting epitope contained in amino acid residues 167 to 588 pneumococcal surface protein A of *Streptococcus pneumoniae*.

4. An isolated polypeptide comprising at least one protection-eliciting epitope contained in amino acid residues 192 to 588 of pneumococcal surface protein A of *Streptococcus pneumoniae*.

5. The protein fragment of claim 1 which is produced recombinantly.

6. The fragment of claim 1 wherein the *Streptococcus pneumoniae* is Rx1.

7. The polypeptide of claim 3 which is produced recombinantly.

8. An isolated pneumococcal surface protein A (PspA) fragment consisting essentially of a C-terminal portion of the PspA protein from amino acid residue 167 or 192 up to and including the amino acid residue 588 and containing at least one protection-eliciting epitope.

9. The polypeptide of claim 4 which is produced recombinantly.

10. A tandem protein fragment comprising a plurality of conjugated molecules, said molecules comprising an isolated pneumococcal surface protein A (PspA) protein fragment corresponding to the amino acid sequence of at least one protection-eliciting epitope located in residues 167 or 192 to 588 of the PspA, each molecule within said plurality of conjugated molecules being derived from different strains of *Streptococcus pneumoniae*.

11. A vaccine against disease caused by pneumococcal infection comprising, as an immunologically-active component, at least one PspA fragment or at least one polypeptide as claimed in any one of claims 1, 3, 4, 8, or 10.

12. The vaccine of claim 11 wherein said PspA protein fragment or polypeptide is conjugated to a carrier protein or bacterial cell having a molecular weight which is greater than that of the PspA fragment or polypeptide.

13. A pneumococcal surface protein A (PspA) fragment as claimed in claim 1 which is an expression product of a recombinant plasmid comprising a DNA molecule having a nucleotide sequence encoding the PspA fragment.

14. An immunological composition comprising the PspA fragment of claim 1 and a suitable carrier or diluent.

15. An immunological composition comprising the PspA fragment of claim 2 and a suitable carrier or diluent.

16. An immunological composition comprising the polypeptide of claim 3 and a suitable carrier or diluent.

17. An immunological composition comprising the polypeptide of claim 4 and a suitable carrier or diluent.

18. An immunological composition comprising the PspA fragment of claim 5 and a suitable carrier or diluent.

19. An immunological composition comprising the polypeptide of claim 7 and a suitable carrier or diluent.

20. An immunological composition comprising the PspA fragment of claim 8 and a suitable carrier or diluent.

21. An immunological composition comprising the polypeptide of claim 9 and a suitable carrier or diluent.

22. An immunological composition comprising the PspA fragment of claim 10 and a suitable carrier or diluent.

23. An immunological composition comprising the PspA fragment of claim 13 and a suitable carrier or diluent.

24. A method of eliciting an immunological response in a host comprising administering the composition of claim 14.

25. A method of eliciting an immunological response in a host comprising administering the composition of claim 15.

26. A method of eliciting an immunological response in a host comprising administering the composition of claim 16.

27. A method of eliciting an immunological response in a host comprising administering the composition of claim 17.

28. A method of eliciting an immunological response in a host comprising administering the composition of claim 18.

29. A method of eliciting an immunological response in a host comprising administering the composition of claim 19.

30. A method of eliciting an immunological response in a host comprising administering the composition of claim 20.

31. A method of eliciting an immunological response in a host comprising administering the composition of claim 21.

32. A method of eliciting an immunological response in a host comprising administering the composition of claim 22.

33. A method of eliciting an immunological response in a host comprising administering the composition of claim 23.

34. An immunological composition comprising the PspA fragment of claim 6 and a suitable carrier or diluent.

35. A method of eliciting an immunological response in a host comprising administering a composition as claimed in claim 34.

* * * * *